(12) United States Patent
Trost

(10) Patent No.: US 6,361,694 B1
(45) Date of Patent: Mar. 26, 2002

(54) ENHANCED BIOMASS DIGESTION THROUGH INTERMITTENT INJECTION OF PROPANE

(76) Inventor: Paul B. Trost, 1511 Washington Ave., Golden, CO (US) 80401

( * ) Notice: Subject to any disclaimer, the term of this patent is extended or adjusted under 35 U.S.C. 154(b) by 0 days.

(21) Appl. No.: 09/603,384

(22) Filed: Jun. 26, 2000

(51) Int. Cl.$^7$ .............................. C02F 3/28; C02F 11/04
(52) U.S. Cl. .................. 210/603; 210/610; 210/613; 210/916
(58) Field of Search ................................ 210/603, 610, 210/611, 613, 916, 631; 435/262, 262.5, 264

(56) References Cited

U.S. PATENT DOCUMENTS

| | | |
|---|---|---|
| 3,242,071 A | 3/1966 | Walker |
| 3,383,309 A | 5/1968 | Chandler |
| 4,198,292 A | 4/1980 | Snider et al. |
| 4,289,625 A | 9/1981 | Tarman et al. |
| 4,311,593 A | 1/1982 | Benjes et al. |
| 4,372,856 A | 2/1983 | Morrison |
| 4,482,458 A | 11/1984 | Rovel et al. |
| 4,511,370 A | 4/1985 | Hunziker et al. |
| 4,655,924 A | 4/1987 | Heijnan |
| 4,713,343 A * | 12/1987 | Wilson, Jr. et al. ......... 210/611 |
| 4,714,796 A | 12/1987 | Senkan |
| 4,780,415 A | 10/1988 | Ducellier et al. |
| 4,826,600 A | 5/1989 | Ely et al. |
| 4,897,195 A | 1/1990 | Erickson |
| 4,983,297 A | 1/1991 | Kaczmarek et al. |
| 5,006,250 A * | 4/1991 | Roberts et al. ............. 210/610 |
| 5,015,384 A | 5/1991 | Burke |
| 5,037,551 A * | 8/1991 | Barkley et al. ............. 210/603 |
| 5,057,221 A * | 10/1991 | Bryant et al. ............... 210/610 |
| 5,116,506 A | 5/1992 | Williamson et al. |
| 5,185,079 A | 2/1993 | Dague |
| 5,232,596 A | 8/1993 | Castaldi |
| 5,298,163 A | 3/1994 | Ehlinger |
| 5,310,485 A | 5/1994 | Roshanravan |
| 5,384,048 A * | 1/1995 | Hazen et al. ................ 210/610 |
| 5,651,890 A | 7/1997 | Trost |
| 5,814,514 A * | 9/1998 | Steffan et al. .............. 435/262 |
| 5,840,571 A * | 11/1998 | Beeman et al. ......... 435/262.5 |
| 5,888,396 A * | 3/1999 | Perriello ..................... 210/611 |

FOREIGN PATENT DOCUMENTS

| EP | 0 241 999 | 10/1987 |
|---|---|---|
| FR | 2 484 990 | 6/1980 |

OTHER PUBLICATIONS

Finney, C.D. and Evans, R.S., Anaerobic Digestion—the Rate Limiting Process and the Nature of Inhibition, Science, vol. 190, p. 1088, (1975).

Butane–Propane News, Jan. 1996 (p. 32).

Methane Production from Waste Organic Matter, Stafford et al., CRC Press (1980).

* cited by examiner

Primary Examiner—Christopher Upton
(74) Attorney, Agent, or Firm—Dorr, Carson, Sloan & Birney, P.C.

(57) ABSTRACT

Anaerobic digestion of a biomass system can be made more effective by intermittently introducing propane from an external source into said biomass system. The propane is preferably introduced into the biomass for about 20% to about 80% of any given time period.

20 Claims, 3 Drawing Sheets

ENHANCED BIOMASS DIGESTION THROUGH INTERMITTENT INJECTION OF PROPANE

BACKGROUND OF THE INVENTION

1. Field of the Invention

Wastewater biomass systems normally consist of a mixture of water, organic matter and a variety of bacterial genera whose food, to a large degree, consists of the organic matter component of the biomass and/or other organic waste materials (e.g., volatile solids). The products of anaerobic digestion of such biomass systems normally consist of: (1) a gas phase primarily comprised of carbon dioxide, methane, ammonia, small amounts of other gases (e.g., hydrogen sulfide and hydrogen) and trace amounts (e.g., less than one tenth of one percent by volume) of certain other gases (e.g., propane), which, in total, constitute what is commonly referred to as "biogas"; (2) a liquid phase (aqueous in nature) in which ammonia, nutrients and a host of organic chemicals and gases and inorganic chemicals are dissolved; and (3) a colloidal phase of suspended solids containing undigested organic and inorganic compounds, synthesized biomass and/or bacterial cells.

Progressive destruction of the organic matter in such biomass systems has been made more efficient by introducing various solubilized nutrients for the bacteria into such systems. Various gases also have been injected into these systems as gas stripping agents. In effect, these gas stripping agents dissolve those biogas molecules (e.g., methane, carbon dioxide, ammonia, hydrogen, hydrogen sulfide, etc.) that are produced as waste products of the bacterial metabolic processes carried out in such biomass systems. These waste product gases are produced within the bacteria cells, permeate their cell walls and collect, in the form of bubbles, on their outer cell wall surfaces.

Nitrogen and hydrogen, obtained from sources outside the biomass system, as well as recirculated biomass product gases (e.g., carbon dioxide, methane and hydrogen), have been used to strip waste product gas bubbles from the bacterial cell walls. Again, the waste product gas molecules on the outer surfaces of the cells are dissolved in the stripper gases. Consequently, newly produced waste product gas molecules are able to leave the outer surfaces of the bacteria cell walls more quickly—and thereby produce more efficient biomass digestive processes.

2. Description of Related Art

Many academic, patent and trade publications have recognized the above-noted biomass gas inhibition problems and have suggested various ways to solve them. For example, within the academic literature, the following articles give some particularly good insights into the nature of these problems. Finney, C. D., and R. S. Evans, Anaerobic Digestion—the Rate Limiting Process and the Nature of Inhibition, Science, 1975, Vol. 190, p. 1088; McCarty, P. L., Anaerobic Waste Treatment Fundamentals, Part I, Public Works, 1964, p. 107; and Obayashi, A. W., and J. M. Gorgan, Management of Industrial Pollutants by Anaerobic Processes in Industrial Waste Management Series, W. James (ed.), Lewis Publishers, Inc., Chelsea, Mich., 1985; and Anaerobic Digestion Processes in Industrial Wastewater Treatment, Stronach, S. M., Rudd, T., and Lester, S. N., Springer-Vertog, Berlin, 1986.

The Finney and Evans article, for example, postulates that the rate controlling step in anaerobic digestion processes of this kind may be the fact that the cells' gaseous waste products (e.g., $CH_4+CO_2$) must eventually undergo a transfer from the system's liquid phase to its gas phase. That is to say that, even though many previous investigators had considered the biological conversion of organic acids (such as acetic acid and propionic acid) into methane and carbon dioxide as being the overall rate controlling reactions, Finney and Evans postulated other rate limiting steps. These authors suggested that the rate of removal of gas bubbles away from bacterial cell walls might constitute the rate limiting step.

Finney and Evans also postulated that, by remaining attached to their cell walls, waste product gas bubbles effectively (a) decrease the cell wall's gas transfer, surface area, (b) decrease the cell wall/gas layer system's overall permeability and (c) reduce the cell's ability to absorb needed nutrients. They also considered the possibility that the presence of certain toxic compounds in the biomass may interfere with a bacterial cell walls' ability to pass dissolved nutrients into the cells.

Many patent references teach various specific processes for stripping gases, such as hydrogen sulfide, from anaerobic cells in digester systems. U.S. Pat. No. 5,651,890 ("the '890 patent", to applicant) is a particularly relevant patent in this regard; hence, its teachings are incorporated herein by reference. The '890 patent teaches that anaerobic digestion of wastewaters can be made more effective by introducing propane gas (from an external source) into the biomass in order to strip bacterial waste product gases such as $H_2S$ from bacteria cell walls. This patent does not however teach or suggest (1) the beneficial effects of stripping $CH_4$ and $CO_2$ gases off of the volatile solids component of the biomass system (and thereby creating more surface area on the volatile solids to which waste product gases can adhere) nor (2) the reduction of $H_2S$ produced in the biogas. Moreover, the '890 patent does not teach or suggest intermittent introduction of propane gas into a biomass in order to make such processes more efficient. Indeed, the '890 patent (see col. 11, line 14) teaches away from the concept of introducing propane intermittently. It also should be noted that the '890 patent also very strongly teaches away from the concept of using propane as a bacterial nutrient (see col. 13, lines 33–53) or having propane interact in any other biological process.

U.S. Pat. No. 4,289,625 (the '625 patent) teaches use of a hybrid, bio-thermal system comprised of an anaerobic digester unit and a thermal gasifier unit. In effect, the anaerobic digester system of the '625 patent achieves greater methane production per unit of feed by "digesting" and "cracking" the anaerobic sludge material and, secondarily, by feeding the thermal gasifier's, gaseous products back to the digester unit as food sources for the microorganisms residing therein. Some of these gaseous products are characterized as "$C_xH_y$" in the '625 patent, but no particular emphasis is laid upon a propane gas component that may fall within the generalized term "$C_xH_y$". This is not surprising because a thermal gasifier such as this would tend to produce an extremely varied source of hydrocarbons due to its "cracking" ability.

U.S. Pat. No. 5,298,163 teaches that a "neutral" gas (no disclosures are made as to the exact identity of such a "neutral" gas) can be introduced in a biodegration process in order to strip or otherwise displace hydrogen sulfide gas from a biomass system but no $H_2S$ reduction in the produced biogas was noted.

U.S. Pat. No. 5,015,384 teaches an anaerobic digestion process that injects "anoxic" gases to strip carbon dioxide gas from a biomass system so that its pH remains neutral or nearly so. This reference states: "The primary requirement is that the gas be anoxic, i.e., not contain oxygen or other constituents toxic to the anaerobic bacteria."

U.S. Pat. No. 4,826,600 teaches a process for altering the pH of a anaerobic system by using methane gas to strip carbon dioxide gas from the system. This process also may employ an "inert" gas to aid in the withdrawal of gaseous products. The preferred "inert" gas is methane.

U.S. Pat. No. 5,185,079 teaches an anaerobic reactor that removes biogas from the top of a reactor and re-introduces it into the bottom of said reactor. This reference also notes the beneficial effects of applying a vacuum during its settling phase to promote removal of gas bubbles attached to bacterial cell walls.

U.S. Pat. No. 4,372,856 discloses a process wherein a sludge is sparged with methane gas in order to stimulate the growth of anaerobic bacteria and, thus, greater production of biogas. This reference also teaches that biogas may be stripped of its "undesired" carbon dioxide and hydrogen sulfide components by passing it through a scrubbing liquid prepared by use of ammonia produced by another phase of the overall process. This reference does not teach reduction of $H_2S$.

Use of propane as a gas stripping agent in anaerobic digesters also is noted in certain trade literature. For example, the January 1996 issue of the trade magazine Butane-Propane News (p. 32) reports that propane can be bubbled through anaerobic digesters to accelerate their reaction rates. The mode of propane injection is not disclosed in this article. Applicant, however, has personal knowledge that the propane used in this process was injected into the biomass system on a substantially continuous basis.

The trade literature also has recognized that some trace amounts (<0.1%) of propane are produced by large scale (municipal) anaerobic digester systems. For example, a leading trade-oriented publication in this area: Methane Production From Waste Organic Matter, by Stafford et al., CRC Press, Inc., Boca Raton, Florida (1980) ("the Stafford reference") states (on page 114) that some "small quantities" of propane may be formed by "polymerization" of methane in an anaerobic digester. It also might be noted that this reference also states that, as far as biogas make up is concerned, anaerobic digesters of this kind usually make 60–70% methane and 30–40% $CO_2$ along with rather small amounts of $H_2S$ and $H_2$. These statements imply that any other gases (e.g., propane) that may be produced by such anaerobic processes are produced in only trace amounts (e.g., <0.1%). Applicant has personally measured the propane content of several such anaerobic digesters prior to the introduction of any external propane source and found that their propane concentrations to be <0.1%.

These academic, patent and trade references indicate that much work has been done to improve the performance of anaerobic digesters—and, indeed, much has been accomplished. However, further improvements in this art are still being sought on many fronts and are always welcome when, in fact, achieved. To this end, applicant's present processes improve the operating performance of anaerobic biomass systems in general, and large scale municipal waste water treatment plants in particular, through use of propane or intermittent injections of a propane-containing gas.

SUMMARY OF THE INVENTION

The inventive concepts of this patent disclosure revolve around the fact that, even though the prior art teaches injection of propane gas into biomass systems in order to strip waste product gases from the exterior of anaerobic bacteria cell walls, the full beneficial value of propane with respect to the metabolic processes of such cells has not been achieved. Indeed, it might even be said that, heretofore, the nutrient properties of propane and/or the utilization of propane in the biological processes of anaerobic bacteria have not been recognized.

Applicant believes that the best evidence for the proposition that intermittently injected propane is acting as a nutrient (or taking part in some other, as yet unknown, biological process) in applicant's process is a well documented lack of mass balance with respect to the injected propane. Applicant has repeatedly found that up to 50% of the injected propane cannot be accounted for in mass balance calculations conducted with respect to processes wherein the propane was introduced on an intermittent basis.

The beneficial effects of the hereindescribed processes are achieved through intermittent, as opposed to continuous, introduction of propane into anaerobic biomass systems. These beneficial effects follow from the fact that, in those periods wherein propane is not introduced, the biomass bacteria have an opportunity to take up the propane through their cell walls and/or to have the propane metabolically interact with the bacteria in some, as yet undefined, manner. Possibly the cell walls serve to better attract the propane under these conditions, and, hence, give it a better opportunity to penetrate the bacteria cell walls and serve as a bacterial nutrient especially for those bacteria involved in the formation of $H_2S$. Conversely, during those periods when the propane is introduced into an anaerobic biomass system, portions of that propane serve primarily as a stripper gas. Thus, applicant's processes improve upon prior art use of propane in biomass systems by aiding those metabolic processes carried out within the interior of the cell walls, while still dealing with those problems associated with the inhibitory effects associated with methane, carbon dioxide, hydrogen sulfide and hydrogen bubble build up on the exterior surfaces of those cell walls.

Applicant also has found that the improved efficiencies of the hereindescribed processes (relative to prior art processes wherein propane is introduced more or less continuously) result, at least in part, from the fact that $H_2$ levels in prior art processes (wherein stripper gases are continuously introduced) are reduced to levels that lead to inhibition of $CH_4$ formation by biochemical conversion of $H_2$ and $CO_2$ to $CH_4$ within the cell walls. Applicant has postulated that intermittent or cyclical addition of propane gives a biomass an opportunity to build up its $H_2$ levels. Apparently, this circumstance facilitates better conversion of $H_2$ and $CO_2$ to $CH_4$. Applicant's experimental work also suggests that, even during periods when no propane is injected, minor stripping of the $H_2$, $CO_2$, and $CH_4$ may still occur (at a diminished rate) as a result of residual dissolved propane coming out of solution and dissolving gas molecules adhering to the outer cell walls of the biomass bacteria.

Conversely, during periods of propane injection, $H_2$, $CO_2$, $CH_4$, etc. are more readily stripped off the exterior surfaces of the bacteria cell walls as well as the outer surfaces of any volatile solids present in the digester system. Thereafter, they are removed from the digester liquid. Applicant is of the further opinion that retention of $CH_4$ and $CO_2$ on the surfaces of volatile solid particles may impede attachment of bacteria on to the surfaces of volatile solids by blocking favorable attachment sites on said solids.

The above-noted decreases in $H_2S$ production by applicant's processes (e.g., decreases of almost 50%) also can be extremely beneficial from a purely economic point of view. This follows from the fact that current $H_2S$ treatment processes usually involve addition of $FeCl_2$ or $FeCl_3$ to large scale waste water treatment plants. For example, $FeCl_3$ costs of over $55,000 per year are typically incurred by waste water treatment plants of about 25 million gallon per day (mg/d) capacities. Tests conducted at the Greeley, Colorado Waste Water Treatment Plant, data showed that $H_2S$ production can be decreased by about 50% through intermittent injection of propane. Applicant has also found that the intermittent propane injection processes of this patent disclosure also result in increased alkalinity of the biomass and increased biological conversion of certain hard to digest hydrocarbons whose degradation is aided by the presence of propane in the system.

Be all that as it may, applicant has found that the prior art practice of injecting propane into biomass systems on a substantially "continuous" basis in order to perform a waste product gas stripping function is not conducive to anaerobic bacteria cell take up of propane as a nutrient. More importantly, applicant has found that when propane is introduced into anaerobic biomass systems on an intermittent basis the operating efficiency of the digestion process is greatly improved. Applicant also has determined that intermittent introduction of propane results in other desired attributes for such biomass systems e.g., increased alkalinity and decreased $H_2S$ levels.

For the purposes of this patent disclosure, the expression "intermittent" basis should be taken to mean that in any given period of time in which an anaerobic digester is operating, propane introduction takes place for about 20% to about 80% of that given period of time. Preferably, the propane injection is continuous during the 20% to 80% subperiod of the given period. This requirement for a 20% to 80% subperiod wherein propane is injected, implies that during another 80% to 20% subperiod of that given period of time, propane is not introduced into the anaerobic digester.

In the more preferred embodiments of this invention, a first time period (in which propane is introduced into the digester and then not introduced into the digester) is followed by a second time period wherein propane introduction again takes place for 20% to 80% of that second time period and does not take place for 80% to 20% of that second time period. In certain even more preferred embodiments of this invention, the second period (of propane injection and non-injection) is followed by third, fourth, fifth, etc. time periods having comparable subperiods wherein propane is injected and then not injected. The summation of these consecutive periods can be termed an overall process period ("overall process period"). Here again, in the case where a series of such consecutive time periods are used, it is preferred that the propane be injected continuously during each of the 20% to 80% subperiods wherein the propane is injected.

In the more preferred embodiments of this invention, there will be from 2 to about 100 consecutive periods wherein propane is injected for about 20% to about 80% (and not injected for about 80% to about 20%) of each of said consecutive periods. Intermittent propane injection programs comprised of about 10 to about 50 consecutive periods (each comprising a period of propane injection and a period of non-injection) are even more highly preferred. In other words, these 2 to about 100 (and preferably 10 to about 50) consecutive periods constitute an overall process period.

Those skilled in this art also will appreciate that most large scale, waste water treatment plants operate on a more or less continuous basis. Thus, when the hereindescribed processes are being used in the context of such a continuous operation, the length of applicant's overall process period will be defined by the summation of the lengths of time for each of the consecutive periods in which propane is injected intermittently during the course of the overall continuous operation.

Next it should be noted that any given time period (wherein propane is injected for a 20% to 80% subperiod, and not injected for a 80% to 20% subperiod), will preferably be from about 30 minutes to about 30 days in length. In certain preferred embodiments of this invention, e.g., operation of municipal waste water treatment plants having capacities of from about 0.5 million gallons per day (mgd) to about 300 mgd, the given time periods (over which propane is injected and not injected) will preferably range from about 4 hours to about 12 hours over an overall process period of at least 1 day. Overall process periods of from 2 to about 365 days duration are even more preferred in the context of large scale (e.g., 10 mgd) municipal waste water treatment plants.

Next, it should be noted that each succeeding time period in any given overall process period can be of the same length, or of a different length, relative to the length of a preceding time period of an overall process period. By way of example only, suppose a given overall process period is comprised of 5 consecutive time periods which are each 8 hours long. Thus, according to applicant's formula, in the first eight hour period, the propane will be injected from about 1.6 hours (20% of 8 hours) to about 6.4 hours (80% of 8 hours). Likewise, in the second eight hour time period, the propane will be injected for about 1.6 hours to 6.4 hours and so on for the third, fourth and fifth time periods. Similarly, in an overall process comprised of a series of 24 hour periods, propane will be injected for a subperiod ranging from 4.8 to 19.2 hours with no propane being injected for a subperiod ranging from 19.2 hours to 4.8 hours of each of the 24 hour periods that constitute the overall process period.

In other embodiments of this invention, the succeeding time periods in an overall process will not be of equal duration. That is to say that each succeeding time period within an overall process period may be substantially longer than, or shorter than, the preceding period. Again, by way of example only, suppose an overall process period of 10 hours total duration is comprised of four consecutive time periods that respectively have durations of one hour, two hours, three hours and four hours. Thus, in the first period (of one hour duration) the propane will be injected for about 12 minutes (20% of 60 minutes) to about 48 minutes (80% of 60 minutes). In the second period (of two hours duration) the propane will be injected for about 24 minutes (20% of 120 minutes) to about 96 minutes (80% of 120 minutes). Following this formula, the propane will be injected for about 36 minutes (20% of 180 minutes) to about 144 minutes (80% of 180 minutes) in the third period and about 48 minutes (20% of 240 minutes) to about 192 minutes (80% of 240 minutes) in the fourth period. In some preferred embodiments of this invention wherein at least five consecutive time periods are employed, at least 20% of said five consecutive periods will be of a different duration (e.g., 1 out of 5 in the case of 5 consecutive time periods).

Next, it should be noted that in one particularly preferred embodiment of this invention, addition of propane during peak heating demand periods is preferred. Typically, in a large scale digester (e.g., 10 mgd), such periods of peak propane demand occur during relatively cooler evening periods—or during peak electrical load periods when heat loss from such digesters is usually greater due to cooler evening temperatures. Thus, one particularly preferred embodiment of this invention involves introducing propane into such large scale plants during non-daylight hours of an overall process period comprised of a series of 12 hour time periods.

Next, it should be noted that the hereindescribed processes involve injection of propane (or a mixture of gases such as air, nitrogen, methane, etc. that contains a propane component). It also should be noted that the primary source of the propane in applicant's processes is not propane obtained from the biogas produced by the process itself. Indeed, applicant has found that very little propane is naturally produced by anaerobic biomass processes in general. Even less is produced by applicant's intermittent propane injection processes. For example, in a series of tests conducted at the Loveland Wastewater Treatment Plant, Loveland, Colorado, applicant determined that the natural level of propane level of this particular plant's biogas (i.e., before introduction of propane according to the teachings of this patent disclosure) was only 0.02 volume percent of the biogas. Thus, in the case of the Loveland, Colorado plant, the extraneous propane introduced into this plant according to applicant's processes, should be intermittently introduced in concentrations such that the biogas product contains more than 0.02 volume percent propane. In any case, in the more preferred embodiments of this invention at least 98% of the propane introduced into those biomass systems operated according to the teachings of this patent disclosure will be obtained from a source other than the biomass system itself.

As a practical matter, however, applicant has determined that the best results for the hereindescribed processes are achieved when propane is intermittently introduced in amounts such that the ratio of propane in the biogas produced is raised from its natural level (e.g., 0.02 volume percent in the case of the Loveland Plant) to about 0.1 to about 5.0 volume percent. Biogas propane concentrations of about 0.5 to about 2.5 volume percent are more preferred. The most preferred propane/biogas concentration is about 1.5 volume percent. Biogas propane concentrations greater than about 5.0 volume percent are not preferred.

Applicant also has found that particularly good biodigestion results are obtained in large scale biomass systems when the concentration of propane gas in the gas injected into the biodigester is about 0.6 to about 4.0 volume percent of the injected gas (e.g., a gas mixture of propane, nitrogen, hydrogen, etc.). Injection of propane in such concentrations will generally produce a biogas product having a propane concentration of from about 0.3 to 2.5 volume percent of the biogas product, Applicant also has found that particularly good results are obtained when the concentration of the propane gas injected into large scale plants is about two and one half times the desired concentration of that biodigester's biogas product. For example if the desired concentration in the biodigester's biogas product is 1.0 volume percent, the concentration of the propane injected into the digester is preferably from about 2.0 to 2.5 volume percent.

Next, it should be noted that the propane-containing gas mixture (from whatever "external" propane source that is being employed) will preferably contain more than about one volume percent propane, and more preferably will contain more than five volume percent propane, and most preferably will contain more than fifty volume percent propane. Bottled propane, liquid propane gas, natural gas (LPG), industrial "by product" propane-containing gases and the like all may be employed, in applicant's processes. Mixtures of gases from such sources also may be employed. Such gases can be injected, sparged, etc. in ways known to those skilled in this art. Those skilled in this art also will appreciate that if bottled, liquid propane is injected into a liquid system it will "flash" into a gas form upon being injected into a liquid system.

Applicant also has found that when propane is introduced intermittently, the overall propane addition can be significantly lowered without sacrificing process efficiency relative to otherwise comparable biomass processes wherein propane is introduced on a substantially continuous basis. Indeed, applicant has found that, in most cases, overall digester efficiency is usually raised when the decreased amounts of propane employed in the present processes are injected on an intermittent basis. By way of a concrete example of this, applicant established that the total amounts of propane used in certain prior art anaerobic processes wherein the propane is employed as a stripper gas (e.g., such as the amounts used in the processes disclosed in the '890 patent wherein propane is introduced continuously in 3% to 15% concentrations as a stripper gas) can be cut by at least about 60% percent without sacrificing the operating efficiency of the digester unit. For example, applicant found that the overall operating efficiency of a process wherein only 2 volume percent propane is intermittently introduced can be as effective as a process wherein propane is continuously introduced at 5 volume percent. This decreased propane requirement represents a significant economic savings. Applicant also has found that introduction of as little as 2.0 volume percent propane, on an intermittent basis, results in a process that has as little as 0.13% propane concentration in its biogas product. That is to say that under these conditions most of the propane was utilized by the bacteria in the biomass system.

Addition of propane to the Greeley anaerobic digester during a first test period was carried out in an intermittent manner (12 hours of propane addition followed by 12 hours of no propane addition) in propane concentrations of 1.8–2.5% by volume. During that first test period, the $H_2S$ concentration was found to decrease from 900 ppm (volume $H_2S$/volume Biogas) to 450 ppm in the biogas. During a second test period no propane was added and the $H_2S$ concentration again increased to 900 ppm. Thereafter, during a third test period, propane addition was again initiated, but in concentrations of 0.6–0.8 volume percent, in 12 hour cycles, e.g., 12 hours on, 12 hours off. During this third test period the $H_2S$ concentration was found to decrease to a 800–850 ppm range. Based upon these observations the following conclusions can be drawn: (1) intermittent addition of propane results in a decrease in $H_2S$ concentration in the produced biogas and (2) a decrease in $H_2S$ concentration appears to be inversely related to the concentration of propane introduced into the digester; higher concentrations is of introduced propane (>1.8%) resulted in approximately a 50% lowering of the $H_2S$ in the biogas, whereas lower concentrations of propane (0.6–0.8%) resulted in only a 5–12% lowering of the $H_2S$ in the biogas. Thus, the effectiveness of applicant's intermittent propane injection methods also can be measured in terms of decreased $H_2S$ concentration in the biogas products of said injection methods.

DESCRIPTION OF PREFERRED EMBODIMENTS

Figure 1:
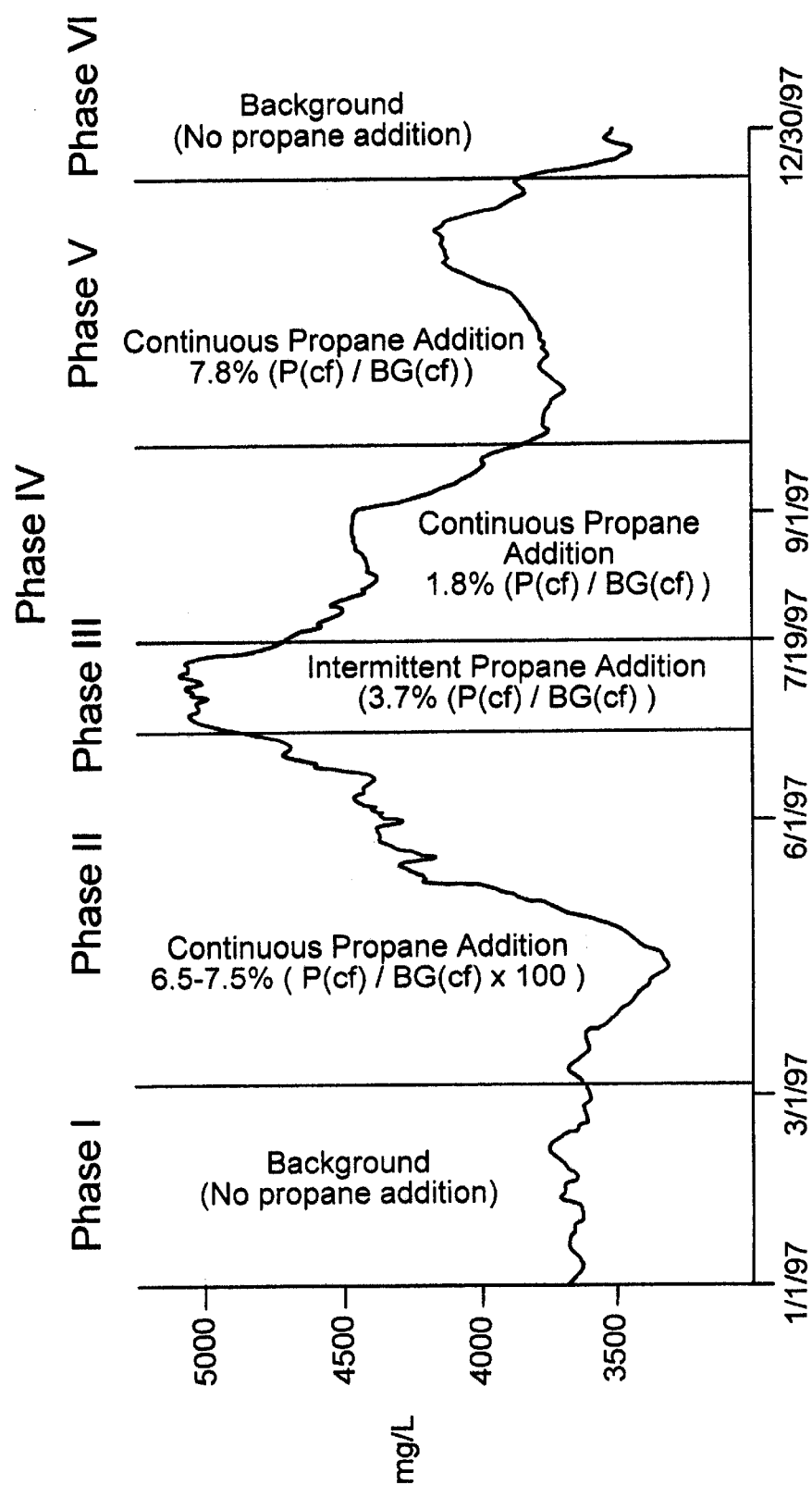
FIG. 1 illustrates increased alkalinity of a biomass system subjected to intermittent propane injection according to the teachings of this patent disclosure.
Figure 2:
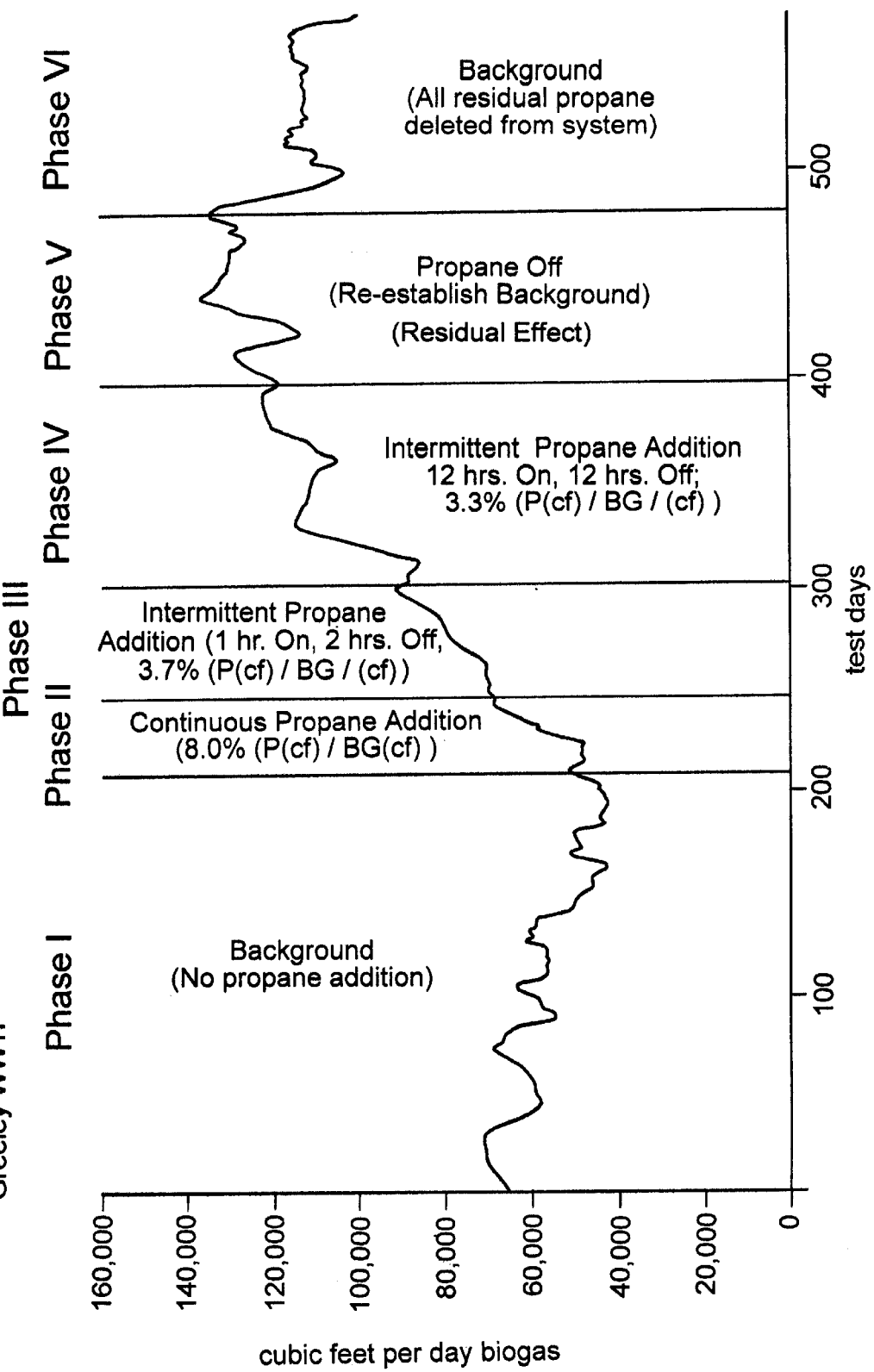
FIG. 2 illustrates increased biogas production through use of intermittent injection of propane.
Figure 3:
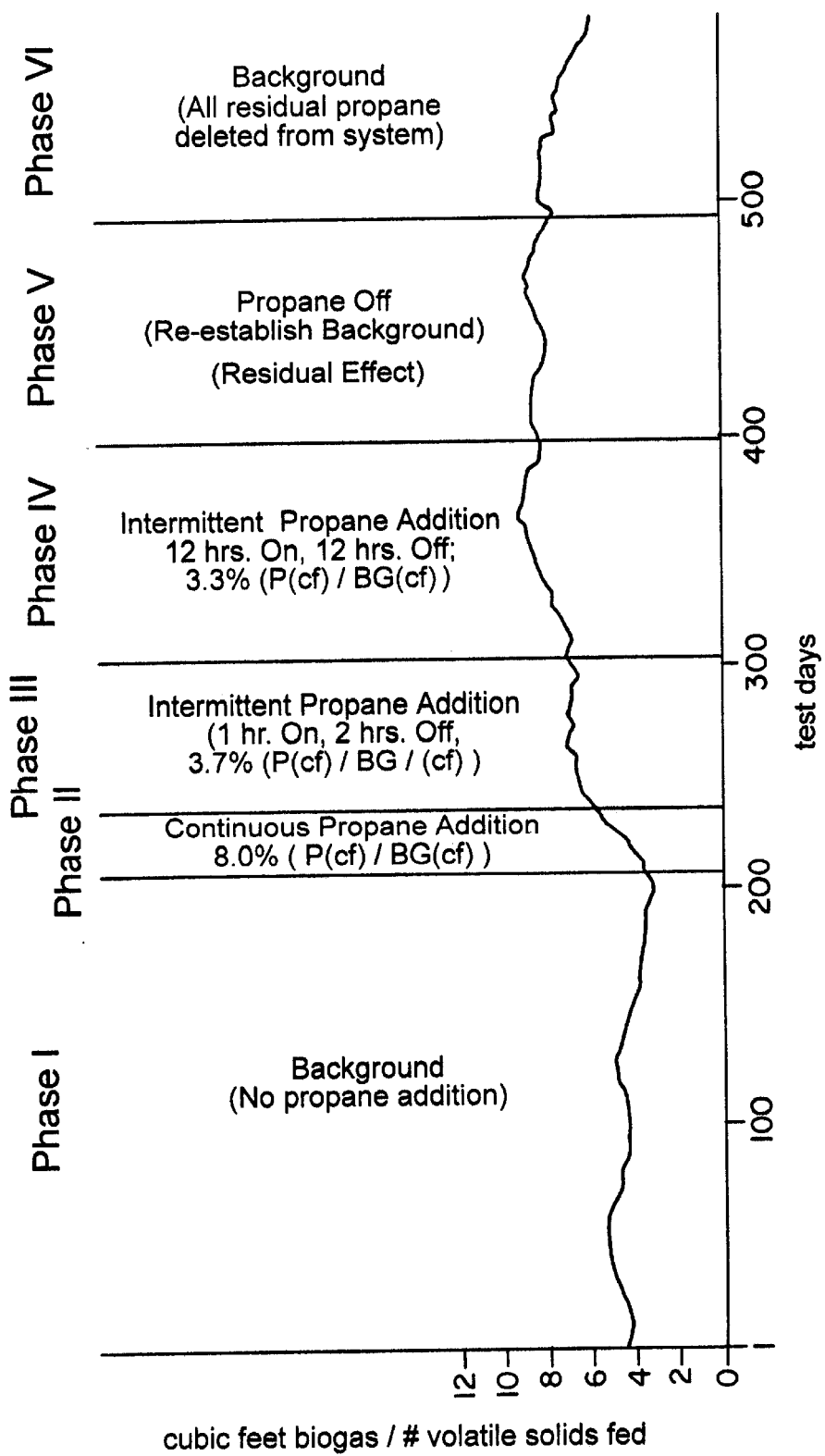
FIG. 3 illustrates increased digestive efficiency through use of intermittent injection of propane.

In order to establish the efficacy of the intermittent propane injection processes of this patent disclosure, applicant conducted a series of comparative tests at the Loveland, Colorado Municipal Wastewater Treatment Plant ("Loveland plant") and at the Greeley, Colorado Municipal Waste Water Treatment Plant ("Greeley plant"). In these comparative tests, propane was not introduced, introduced continuously, and introduced intermittently according to the teachings of this patent disclosure. Several different criteria were employed to evaluated the tests results.

One such criterion was to compare the amount (by volume) of propane introduced into the biomass to the amount (by volume) of propane in the biogas given off by the biomass. Presumably, the difference in these values represents, for the most part, propane that was used by the bacteria as a nutrient—or used in some other, as yet undefined, biological process carried out by the cells in the biomass. For example, in one such test at the Greeley plant, a total of 6325 cubic feet of propane was injected into the biomass system on an intermittent basis (a series of given time periods comprised of 12 hour propane injection subperiods and 12 hour non-injection subperiods) over a seven day overall process period. Only 2075 cubic feet (or about 33 percent) of the 6325 cubic feet of propane originally injected in this test could be accounted for in the biogas product. In a second test conducted at that same plant, a total of 5142 cubic feet of propane gas was intermittently injected on a similar 12 hour propane injection/12 hour non-injection period cycle basis over a 14 day overall process period. Only 2580 cubic feet (or about 50 percent) of the originally injected propane was contained in the biogas product. In a third test, a total of 2468 cubic feet of propane was again injected on a 12 hour cycle basis over a seven day overall process period. Only 663 cubic feet (or about 27 percent) of the original propane could be accounted for in the biogas product. During a fourth test at the Greeley plant, a total of 1800 cubic feet of propane was intermittently injected on a 12 hour cycle basis and only 115 cubic feet (or about 6.4 percent) of the original propane was found in the biogas product.

Other tests employed operating efficiency with respect to propane inputs as a criterion for evaluating applicant's intermittent propane injection processes. To this end, the number of cubic feet of propane ("P(cf)") added at the point of propane introduction divided by the cubic feet of biogas produced by the digester (BG(cf)) during a given time period was the specific test criterion. This cubic feet of propane per cubic feet of biogas produced criterion is designated as "P(cf)/BG(cf)" in this patent disclosure. In effect, it tests the efficiency of a volume of propane in producing a volume (cf) of biogas. Stated as a percentage, this efficiency is P(cf)×BG(cf)×100=percentage. Thus, a process using less propane to produce a given volume of biogas has a lower P(cf)/BG(cf)×100 value relative to a process using more propane to get the same biogas production results. Using injection methods comparable to those used in the test processes previously noted, applicant has found that this P(cf)/BG(cf)×100 value can be as low as about 0.5% in intermittent injection processes and still obtain good operating results. Applicant also established that P(cf)/BG(cf)×100 values greater than about 5.0% are not needed and hence, for largely economic reasons, are not preferred. In any case, as previously noted, the P(cf)/BG (cf)×100 values produced by applicant's intermittent injection processes were consistently much lower (e.g., 60% lower) than those P(cf)/BG(cf)×100 values produced by continuous propane injection processes under otherwise comparable conditions, e.g., such as those taught in the '896 patent.

Applicant also evaluated the operating efficiency of the Greeley plant and the Loveland plant on the basis of the changes produced in the alkalinities of these biomasses by (1) intermittent propane injection, (2) no propane introduction and (3) continuous propane injection. These tests also employed a cubic feet of biogas per pound of volatile solids fed ("cf/#VS") as yet another test criterion. For example, in a series of tests conducted at the Greeley plant, continuous injection of a gas containing 3.1% propane, over a 30 day period, resulted in a biomass having an alkalinity of 4500 mg/l. Under these test conditions, the cf/#VS ratio was 6.0. By way of comparison, intermittent addition of propane (even at a lower, i.e., 2.3% propane concentration), over a 31 day test period, on a 12 hour cycle basis (i.e., propane injection for 12 hours, followed by a 12 hour period in which propane was not injected), resulted in a biomass having an alkalinity of 6000 mg/l and a cf/#VS ratio of 7.9. These two comparative values each represent a significant increase in biomass operating efficiency.

By way of a further example of the advantages of applicant's processes, FIG. 1 compares the effects of: (1) not introducing propane in a Loveland plant test, (2) continuous propane injection therein and (3) intermittent propane injection therein. This test covered about a one year test period. The tests that produced the curve shown in FIG. 1 used the alkalinity of the biomass system as a test performance criterion. The first test period (i.e., Jan. 1, 1997 to about Mar. 1, 1997) is designated in FIG. 1 as Phase I. Phase I is characterized by the fact that no extraneous propane was injected into the system. Phase I shows an average alkalinity of about 3700 mg/L. Phase II shows the results of injecting propane into that biomass on a continuous basis. The (P(cf)/BG(cf)) values range from about 6.5 to about 7.5 percent. The resulting alkalinity level of this system averaged about 4500 mg/L. Phase III shows the results of adding propane on an intermittent basis. The (P(cf)/BG(cf)) level was 3.7%. The resulting alkalinity level (mg/L) averaged over 5000 mg/L. This was the highest relative level of this overall test; hence, it demonstrates the increased effectiveness of applicant's processes. Phase IV and Phase V respectively show the results of continuously introducing propane 1.8% and 7.8% cf/vol.×100 (P(cf)/BG(cf)) levels. Phase VI depicts the situation where, once more, propane no longer resides in the system.

It might also be noted here that the Manual of Practice No. 16, Anaerobic Sludge Digestion, (1987), page 6, states: "Digesters should have bicarbonate alkalinity levels of 2500 to 5000 mg/l to neutralize volatile acids and prevent a drop in pH." This would indicate that the alkalinity increase achieved by the hereindescribed processes is very beneficial since such processes provide an operating margin of greater than 5000 mg/l.

In yet another test conducted at the Greeley, Colorado plant, intermittent propane injection over a 26 day overall process period (on a 12 hour cycle basis) produced an average alkalinity increase from 5200 mg/l to 6000 mg/l relative to a continuous propane injection process. Moreover, a net biogas production increase of more than 20% was produced. A 40% reduction in $H_2S$ and an overall operating efficiency increase of almost 50% also was achieved.

In other tests conducted at the Greeley plant, the results of not introducing propane, continuous introduction of propane and intermittent introduction of propane were compared. FIGS. II and III depict the results of these comparative tests. For example, FIG. II depicts the results of a series of tests wherein biogas production (expressed in cubic feet of biogas produced per day) was used as a test criterion. FIG. II shows the lowest biogas production in Phase I wherein no propane was added. Phase II depicts the results of continuous propane injection at a 8.0% (P(cf)/BG(cf)) level. Phase III depicts the biogas production level produced by an intermittent propane injection program having a one hour on, two hours off, injection mode at a 3.7% (P(cf)/BG(cf)) level of propane usage. Phase IV depicts the biogas production level (cubic feet of biogas produced per day) produced by a intermittent propane injection program having a 12 hours on, 12 hours off injection mode at a 3.3% level of propane usage. A comparison of Phases IV and V shows the better results produced by a 12 hour on/12 hours off propane injection mode. Phases V and VI depict the results of reverting to a mode of operation in which no propane was injected so that, eventually, virtually all residual propane is removed from the system, FIG. III depicts the results of a series of tests wherein cubic feet of biogas per pound of volatile solids fed (BG (cf)/#VS) is used as a test criterion. The Phase III results show that the intermittent propane injection at a 3.7% (P(cf)/BG(cf)) level produces better BG(cf)/#VS results relative to no propane injection (Phase I) and continuous propane injection (Phase II). FIG. III also shows that applicant's 12 hour on/12 hour off mode of intermittent injection during Phase IV produces better results even at the 3.7% level mode of injection, shown in Phase IV.

In other tests at these plants, applicant's intermittent addition processes were tested for given periods ranging from one half hour on/one half hour off, to a maximum of 150 days on/150 days off. Examples of some specific comparisons are given in examples 1 through 5.

EXAMPLE 1
LOVELAND, COLORADO WWTP

| LOVELAND, COLORADO WWTP | |
|---|---|
| Continuous Propane Injection: | alkalinity 4350 mg/l; CF/#VS fed 15 |
| Intermittent Injection 12 ON/12 OFF: | alkalinity 4950 mg/l; CF/#VS fed 20 |

EXAMPLE 2
GREELEY, COLORADO WWTP

| GREELEY, COLORADO WWTP | |
|---|---|
| Continuous Propane Injection: | alkalinity 4400 mg/l; CF/VS fed 5 |
| Intermittent Injection 1 ON/2 OFF: | alkalinity 4600 mg/l; CF/VS fed 7 |
| Intermittent Injection 12 ON/12 OFF: | alkalinity 6000 mg/l; CF/VS fed 8.5 |
| Intermittent Injection | alkalinity 6000 mg/l; |
| 90 days of 12 ON/12 OFF, then 60 days OFF: | CF/VS fed 8.5 |

EXAMPLE 3

As part of another field testing program, the biogas from the Loveland plant was individually analyzed before propane from an external source was introduced. The "natural" composition of the plant's biogas was as indicated in Table I.

TABLE I

| COMPONENTS | NORM. MOLE % |
|---|---|
| HYDROGEN | 0.02 |
| OXYGEN/ARGON | 0.01 |
| NITROGEN | 0.15 |
| CO2 | 38.73 |
| METHANE | 61.07 |
| ETHANE | 0.00 |
| PROPANE | 0.02 |
| ISOBUTANE | 0.00 |
| N-BUTANE | 0.00 |
| ISOPENTANE | 0.00 |
| N-PENTANE | 0.00 |
| HEXANES+ | 0.00 |
| TOTAL | 100.00 |

The main point to be made here is that the normal or "natural" level of propane in this plant's biogas is 0.02 mole percent. Those skilled in this art will appreciate that such low propane concentrations are not at all atypical for large scale municipal wastewater digestion systems.

EXAMPLE 4

Other tests conducted at the Loveland plant introduced a propane-containing gas into this biodigester on a continuous basis to produce about a 7.5 percent (P(cf)/BG(cf)) level during the period of May 2–Jun. 14, 1997. Subsequently the propane gas was introduced on an intermittent basis (12 hours on and 12 hours off) during the period of Jul. 7–Jul. 19, 1997 at a 3.7% (P(cf)/BG(cf)) level.

A comparison of the results of these tests is shown below:

| Method of Propane Addition | Propane P(cf)/ BG(cf) × 100 | Alkalinity | BG(cf)/#VS fed |
|---|---|---|---|
| Continuous | 7.5 | 4350 | 15 |
| Intermittent | 3.7 | 5100 | 22 |

Thus, the intermittent addition of propane at about a 50% decreased value increased the operating efficiency of the digester (as measured by both an increase in alkalinity and an increase in BG(cf)/#VS fed ratio). These increases demonstrate both the technical and economic advantages of intermittent propane addition relative to a continuous mode of propane addition.

Thus, while applicant's invention has been described with respect to various theories, and a spirit which is committed to the concept of introducing propane and/or a propane-containing gas mixture into a biomass undergoing anaerobic digestion on an intermittent basis, it is to be understood that this invention is not limited thereto; but rather only should be limited by the scope of the following claims.

Thus, having disclosed this invention, what is claimed is:

1. A process for anaerobic digestion of a biomass, said process comprising intermittently introducing propane into said biomass.

2. The process of claim 1 wherein the propane is introduced into the biomass for about 20% to about 80% of a given time period and not introduced for about 80% to about 20% of that given time period.

3. The process of claim 1 wherein the propane is introduced into the biomass for about 20% to about 80% of a given time period of from about 30 minutes to about 30 days and not introduced for about 80% to about 20% of that given time period.

4. The process of claim 1 wherein the propane is introduced into the biomass for about 20% to about 80% of a given time period of from about 1 hour to about 12 hours and not introduced for about 80% to about 20% of that given time period.

5. The process of claim 1 wherein the propane is introduced into the biomass for about 20% to about 80% of from 2 to about 100 consecutive given time periods, each of said consecutive time periods having a duration of 30 minutes to 30 days, and not introduced for about 80% to about 20% of each of said consecutive time periods.

6. The process of claim 1 wherein the propane is introduced into the biomass for about 20% to about 80% of from 2 to about 100 consecutive given time periods, each of said consecutive time periods having a duration of 30 minutes to 30 days, and not introduced for about 80% to about 20% of each of said consecutive time periods and wherein each of said consecutive time periods is of substantially the same length.

7. The process of claim 1 wherein the propane is introduced into the biomass for about 20% to about 60% of from 2 to about 100 consecutive given time periods, each of said consecutive time periods having a duration of 30 minutes to 30 days, and not introduced for about 80% to about 20% of each of said consecutive time periods and wherein each of said consecutive time periods is of a different length.

8. The process of claim 1 wherein the propane is introduced into the biomass for about 20% to about 80% of from 2 to about 100 consecutive given time periods, each of said consecutive time periods having a duration of 30 minutes to 30 days, and not introduced for about 80% to about 20% of each of said consecutive time periods and wherein at least 20% of said consecutive time periods is of a different length.

9. The process of claim 1 wherein the propane is introduced into the biomass for about 20% to about 80% of from 2 to about 100 consecutive given time periods, each of said consecutive time periods having a duration of about 1 hour to about 12 hours, and not introduced for about 80% to 20% of each of said consecutive time periods.

10. The process of claim 1 wherein the propane is introduced into the biomass for about 20% to about 80% of from 2 to about 100 consecutive given time periods, each of said consecutive time periods having a duration of about 1 hour to about 12 hours, and not introduced for about 80% to 20% of each of said consecutive time periods and wherein each of said consecutive time periods is of substantially the same length.

11. The process of claim 1 wherein the propane is introduced into the biomass for about 20% to about 80% of from 2 to about 100 consecutive given time periods, each of said consecutive time periods having a duration of about 1 hour to about 12 hours, and not introduced for about 80% to 20% of each of said consecutive time periods and wherein each of said consecutive time periods is of a different length.

12. The process of claim 1 wherein the propane is introduced into the biomass for about 20% to about 80% of from 2 to about 100 consecutive given time periods, each of said consecutive time periods having a duration of about 1 hour to about 12 hours, and not introduced for about 80% to 20% of each of said consecutive time periods and wherein at least 20% of said consecutive time periods is of a different length.

13. The process of claim 1 wherein the volume of propane introduced to the volume of biogas produced is from about 0.5% to about 5.0%.

14. The process of claim 1 wherein the concentration of propane introduced is about two and one half times the concentration of propane in the biogas produced.

15. The process of claim 1 wherein the $H_2S$ concentration of a biogas product of said process is lowered relative to a process wherein the propane is injected on a continuous basis.

16. A process for lowering the $H_2S$ concentration of a biomass, said process comprising intermittently introducing propane into said biomass.

17. The process of claim 16 wherein the propane is introduced into the biomass for about 20% to about 80% of a given time period and not introduced for about 80% to about 20% of that given time period.

18. The process of claim 16 wherein the propane is introduced into the biomass for about 20% to about 80% of a given time period of from about 1 hour to about 12 hours and not introduced for about 80% to about 20% of that given time period.

19. The process of claim 16 wherein the propane is introduced into the biomass for about 20% to about 80% of from 2 to about 100 consecutive given time periods, each of said consecutive time periods having a duration of 30 minutes to 30 days, and not introduced for about 80% to about 20% of each of said consecutive time periods and wherein each of s aid consecutive time periods is of substantially the same length.

20. The process of claim 16 wherein the propane is introduced into the biomass for about 20% to about 80% of from 2 to about 100 consecutive given time periods, each of said consecutive time periods having a duration of 30 minutes to 30 days, and not introduced for about 80% to about 20% of each of said consecutive time periods and wherein each of said consecutive time periods is of a different length.

* * * * *